(12) United States Patent
Das et al.

(10) Patent No.: US 7,291,353 B2
(45) Date of Patent: Nov. 6, 2007

(54) **ANTI-PEPTIC ULCER ACTIVITY OF AN EXTRACT OF A FLOWER OF *WOODFORDIA FRUTICOSA***

(75) Inventors: Pratap K. Das, Kolkata (IN); Niranjan P. Sahu, Kolkata (IN); Sukdeb Banerjee, Kolkata (IN); Suchandra Sett, Kolkata (IN); Suchandra Goswami, Kolkata (IN); Samir Bhattacharya, Kolkata (IN)

(73) Assignee: Council of Scientific and Industrial Research, New Dehli (IN)

( * ) Notice: Subject to any disclaimer, the term of this patent is extended or adjusted under 35 U.S.C. 154(b) by 275 days.

(21) Appl. No.: 11/205,146

(22) Filed: Aug. 17, 2005

(65) Prior Publication Data
US 2006/0040005 A1 Feb. 23, 2006

Related U.S. Application Data

(62) Division of application No. 10/397,194, filed on Mar. 27, 2003, now abandoned.

(60) Provisional application No. 60/367,490, filed on Mar. 27, 2002.

(51) Int. Cl.
*A01N 65/00* (2006.01)
(52) U.S. Cl. .................. 424/778; 424/725; 514/925; 514/927
(58) Field of Classification Search ............... None
See application file for complete search history.

(56) References Cited

U.S. PATENT DOCUMENTS

| 5,843,987 | A | 12/1998 | Rajagopalan et al. |
| 6,080,401 | A | 6/2000 | Reddy et al. |
| 6,455,077 | B2 | 9/2002 | Katiyar et al. |

FOREIGN PATENT DOCUMENTS

JP 07126144 A 5/1995

OTHER PUBLICATIONS

Yoshida, Takashi et al., Chemical & Pharmaceutical Bulletin (1991), 39(5), 1157-62. Woodfordin D and oenothein A, trimeric hydrolyzable tannins of macro-ring structure with antitumor activity, Abstract.

Nair, A.G.R. et al., Indian Journal of Pharmacy (1976), 38(4): 110-111. Polyphenols of the flowers of *Woodfordia fruticosa*.

Pavia, D.L. et al., Introduction to Organic Laboratory Techniques, Third Edition, 1988. Saunders College Publishing, U.S.A. Chapter Technique 5: Extraction, The Separatory Funnel, Drying Agents, pp. 541-550.

Green, J., The Herbal Medicine-Maker's Handbook: A Home Manual, 2000. The Crossing Press, U.S.A. Chapter 5: The Extraction Process, pp. 74-77; and, Chapter 6: Solvents, pp. 80-98.

*Primary Examiner*—Michele Flood
(74) *Attorney, Agent, or Firm*—Buchanan, Ingersoll & Rooney, PC

(57) ABSTRACT

A pharmaceutical composition comprising an effective amount of an extract or lyophilized extract or at least one bioactive fraction obtained from the plant *Woodfordia fruticosa* along with one or more pharmaceutically acceptable additives/carriers for treating ulcer caused by the conditions such as stress induced ulcer, peptic ulcer, cold restraint induced ulcer, drug induced ulcer and acid induced ulcer, also used as specific inhibitor of gastric $H^+$, $K^+$-ATPase and anti-*Helicobacter pylori* activity.

14 Claims, No Drawings

ANTI-PEPTIC ULCER ACTIVITY OF AN EXTRACT OF A FLOWER OF *WOODFORDIA FRUTICOSA*

CROSS-REFERENCE TO RELATED APPLICATIONS

This application is a divisional of application Ser. No. 10/397,194, filed Mar. 27, 2003, now abandoned which claims the benefit of provisional Application No. 60/367,490, filed Mar. 27, 2002, both hereby expressly incorporated by reference in their entireties and relied upon.

BACKGROUND OF THE INVENTION

1. Technical Field of the Invention

The present invention relates to a pharmaceutical composition comprising an effective amount of an extract or lyophilized extract or at least one bioactive fraction obtained from plant *Woodfordia fruticosa* along with one or more pharmaceutically acceptable additives/carriers. The present invention particularly provides a composition for treating ulcer caused by the conditions caused by stress induced ulcer, peptic ulcer, cold restraint induced ulcer, drug induced ulcer and acid induced ulcer and also the composition is used as specific inhibitor of gastric $H^+$, $K^+$-ATPase.

2. Background and Prior Art References

Traditional herbal preparations are known for centuries to protect against peptic ulcer diseases, the aetiopathological basis of which were not known in those periods. Current day knowledge about the underlying biochemical mechanism for most of the gastric ulcers and majority of the duodenal ulcers deserve appropriate consideration and due weightage while consolidating the claim regarding the efficacy of a plant extract.

In a Program on 'Discovery, Development & Commercialization of New Bioactive & Traditional Preparations', coordinated by Council of Scientific Research, the Applicant has been collecting, extracting and screening different potential plants and their parts for their bioefficacy against various diseases. Gastric ulcer is one such disease. Based on screening through appropriate experimental model(s), the applicant has selected a plant flower as our target for the development of an effective anti ulcer medicine. This invention envisages to claim the potential of an extract obtained from the flower of *Woodfordia fruticosa* to act as an effective therapy against peptic ulcer diseases.

Reported Medicinal Use:

The plant *Woodfordia fruticosa* Kurz. Syn. *W. floribunda* Salisb popularly known in regional languages as "Dhatki" is a much branched shrub with fluted stems and long, spreading branches, grows to a maximum height of 7 m, and occurs throughout North India, ascending to an altitude of about 1,500 m in the Himalayas [Chadha, Y. R. (ed.), *The Wealth of India, Raw Materials*, Vol. X (1976), Council of Scientific & Industrial Research, New Delhi, pp 586-687]. It is sometimes cultivated in gardens for its flowers. The plant bears numerous flowers, brilliant red in dense axillary paniculate-cymose clusters. The flowers yield a red dye and are employed throughout India for dying fabrics.

The medicinal values of the plant and its parts indicate that the leaves of *Woodfordia fruticosa* possess antibiotic activity in vitro against *Micrococcus pyogens* var. *aureus* as well as sedative properties [Dhar, M. L., Dhar, M. M., Dhawan, B. N., Mehrotra, B. N. and Ray, C., *Ind. J. exp. Biol.* 6, 232 (1968); Paris, R. R. and Jacquemin, H., *Fitoterapia*, 47, 51 (1976); Kadota, S., Takamori, Y., Kikuchi, T., Motegi, A. and Ekimoto, H., *Chem. Pharm. Bull.* 38, 2687 (1990)], and are reported to be used as a folk medicine in India and Nepal. Methanol and water extracts of the leaves of this plant inhibits DNA topoisomerase II [Chen, G. L. and Liu, L. F. *Annu. Rep. Medicinal Chemistry*, 21, 257 (1986].

A preparation consisting of dried fruits, flowers, buds and broken pieces of inflorescences are commercially used in the management of bowel complaints, haemorrhages, menorrhagia and seminal weakness. An extract of the whole plant was found to stimulate the contraction of the intestinal loop, show antipyretic action [Chadha, Y. R. (ed.), *The Wealth of India, Raw Materials*, Vol. X (1976), Council of Scientific & Industrial Research, New Delhi, pp 586-687].

The dried flower of this plant are reported to be used for the treatment of haemorrhoids, dysentery, and liver diseases [[Chadha, Y. R. (ed.), *The Wealth of India, Raw Materials*, Vol. X (1976), Council of Scientific & Industrial Research, New Delhi, pp 586-687; Dhar, M. L., Dhar, M. M., Dhawan, B. N., Mehrotra, B. N. and Ray, C., *Ind. J. exp. Biol.* 6, 232 (1968); Kirtikar, K. R. and Basu, B. D., Indian Medicinal Plants (Eds. Blatter, E., Caius, J. F. and Mhaskar, K. S.), Vol. II, Publishers: Lalit Mohan Basu, Allahabad, India (1935), p. 1074].

The dried flowers are also credited with stimulant and astringent properties. They are often added to the Ayurvedic Arishtas to cause alcoholic fermentation. Powdered dried flowers when sprinkled over ulcers and wounds, diminish discharge and promote granulation. A paste of the flower is reported to be used for the treatment of coughs. An ointment containing this flower was also used in the pustules of smallpox. An extract of the flowers shows activity against *Helminthosporium sativum* [Chadha, Y. R. (ed.), *The Wealth of India, Raw Materials*, Vol. X (1976), Council of Scientific & Industrial Research, New Delhi, pp 586-687; Kirtikar, K. R. and Basu, B. D., Indian Medicinal Plants (Eds. Blatter, E., Caius, J. F. and Mhaskar, K. S.), Vol. II, Publishers: Lalit Mohan Basu, Allahabad, India (1935), p. 1074]. The flowers are reported to be gathered and sucked by children for sweet nectar. They are believed to be eaten, in Madhya Pradesh, and in West Bengal are employed for making a cooling drink [Bhargava, J. *Bombay nat. Hist. Soc.*, 56, 26 (1959); Desai et al. Indian J, Chem. 9, 611 (1971)].

Strategy & Approach Plan:

The concept of management of peptic ulcer diseases is fast changing. Traditionally, treatment was based on the principle that excessive secretion of acid was the sole cause of ulcer symptoms. Later on, a proposed role of psychological stress also gained wide acceptance. Ulcer formation is currently viewed as an interactive process that results from an imbalance of 'aggressive factors' like acid, pepsin, smoking, alcohol, pain killer etc. and 'defensive factors' like mucin, bicarbonate, milk etc. [Hirschowitz, B. L., Keeling, D., Lewin, M., Okabe, S., Parsons, M., Sewing, K. Wallmark, B. and Sachs, G., *Dig. Dis. Sci.*, 40, 3S (1995)].

It was established in the first quarter of the last century that gastric acid is secreted by a class of gastric cells called parietal cells while the physiological basis of obligatory requirements of $K^+$ and $Ca^{2+}$ in gastric HCl secretion and regulation came into our knowledge-base in the middle of twentieth century [Modlin, I. M., *Surg. Gyneol. Obstet.*, 170, 81 (1990).

The role of histamine, gastrin and acetylcholine in controlling gastric acid secretion was understood only around the third quarter of last century and this triggered the designing of chemical molecules acting as blockers of such receptors giving rise to functionally effective anti-ulcer drugs [Prinz. C., Kajimura, M., Scott, D., Helander, H., Shin, J., Besancon, M., Bamberg, K., Hersey, S. and Sachs, G., *Yale J. Biol. Med.* 65, 577 (1992)].

That an enzyme known as 'Gastric Proton Pump' is the final common mediator of HCl transport in the stomach lumen was accepted only in 1980s, paving the way for the advent of omeprazole era [Sachs, G., *Ann. Rev. Pharmacol. Toxicol,* 28, 269 (1998). Finally around 1990s, a bacterium called *Helicobacter pylori* was shown to be responsible for peptic ulcer and perhaps gastric carcinoma [Adrian Lee and Francis Megraud (eds) *Helicobacter pylori: techniques for clinical diagnosis & basic research*, W. B. Saunders Company Ltd. 1996].

All these discoveries are being given appropriate consideration in delineating the claim about the efficacy of this single herbal extract. The applicant anticipates bringing in a new generation of herbal medicine in the horizon. Since sufficient tools and knowledge are available today to come very close to identifying the site of action of any unknown principle(s) with a specific mechanism, and since it is imperative that the specific site of action of a new drug be shown before it can be accepted, the applicant has carefully selected four experimental models so as to cover majority of the aetiological factors responsible for the pathogenesis of peptic ulcer diseases.

Objects of the Invention

The main object of the invention is to provide a pharmaceutical composition for treating peptic ulcer and related ulcerical conditions.

Another object of the invention is to provide a pharmaceutical composition comprising lyophilized extract or bioactive fractions obtained from plant *Woodfordia fruticosa* for the treatment of peptic ulcer caused by various conditions.

Still another object of the present invention is to provide a method of treating ulcers caused by the conditions selected from stress induced ulcer, peptic ulcer, cold restraint induced ulcer, drug induced ulcer and acid induced ulcer.

Yet another object of the invention is using the composition for inhibiting gastric $H^+$, $K^+$-ATPase activity.

Still another object of the invention is to provide a process for preparing lyophilized and bioactive fractions from the flowers of plant *Woodfordia fruticosa*.

SUMMARY OF THE INVENTION

Accordingly, the present invention provides a pharmaceutical composition comprising an effective amount of an extract or lyophilized extract or at least one bioactive fraction obtained from plant *Woodfordia fruticosa* along with one or more pharmaceutically acceptable additives/carriers. The present invention particularly provides a composition for administering to treat ulcer caused by the conditions selected from stress induced ulcer, peptic ulcer, cold restraint induced ulcer, drug induced ulcer and acid induced ulcer and also used as specific inhibitor of gastric $H^+$, $K^+$-ATPase.

DETAILED DESCRIPTION OF THE INVENTION

In accordance to the objectives, the present invention provides a pharmaceutical composition comprising an effective amount of an extract or lyophilized extract or at least one bioactive fraction obtained from plant *Woodfordia fruticosa* along with one or more pharmaceutically acceptable additives/carriers.

One embodiment of the invention provides a composition for administering to subjects suffering from ulcers caused by the conditions selected from stress induced ulcer, peptic ulcer, cold restraint induced ulcer, drug induced ulcer and acid induced ulcer.

Another embodiment, the said composition is used as specific inhibitor of gastric $H^+$, $K^+$-ATPase.

Still another embodiment, the subject is mammal including human being.

Still another embodiment, the amount of extract administered is in the range of 50- to 200 mg/kg body weight/day, wherein, the extract is lyophilized aqueous alcoholic extract and designated as A-002.

Another embodiment provides a composition contain effective amount of bioactive fraction which is administered in the range of 20 to 100 mg/kg body weight/day.

Still another embodiment, the bioactive fraction is selected from a group consisting of bioactive fractions designated as F-006 and F-007.

Another embodiment, the composition can be in the form of tablets, capsules, syrup or by any other form known in the art and is administered orally, intramuscularly, and by any other conventional methods.

Yet another embodiment, the composition may be used for therapeutic as well as prophylactic treatment of peptic ulcer.

Yet another embodiment, the composition may be administered as a single bolus dose or a multiple doses.

One more embodiment of the present invention provides a method of treating a subject for ulcers and related diseases, said method comprises administering an effective amount of a pharmaceutical composition comprising extract or bioactive fractions obtained from plant *Woodfordia fruticosa* along with one or more pharmaceutically acceptable additives/carriers One more embodiment of the invention provides a process for the isolation of extract or bioactive fractions from plant *Woodfordia fruticosa*, especially from the flowers, said process comprising the steps of:

i. collecting the flowers during the month of February and March of the year, drying in shade, and powdering the flower, ii. extracting the powdered flowers with a mixture of water and alcohol in the ratio of 1:1, iii. concentrating the aq.alcoholic extract under reduced pressure at 30° C. and iv. finally freeze-drying to obtain a powder designated as A-002, v. further partitioning the residue with n-butanol and water to obtain two fractions, the n-butanol soluble fraction and the aqueous part, vi. concentrating the fractions under reduced pressure and finally freeze-drying to yield n-butanol soluble fraction designated as F-006 and aqueous fraction designated as F-007.

EXAMPLES

The following examples are intended to demonstrate some of the preferred embodiments and in no way should be construed so as to limit the scope of the invention. Any person skilled in the art can design more formulations, which may be considered as part of the present invention.

Example 1

Collection, Extraction and Fractionation:

The present invention consists of collection of the flowers during the month of February and March of the year, drying in shade, extracting the powdered flowers with a mixture of water or alcohol in the ratio of 1:1, concentrating the extract under reduced pressure at 30° C. and finally freeze-drying to a powder (A-002). Further partition of the extract with n-butanol and water furnished two fractions, the n-butanol soluble fraction and the aqueous part. Both the fractions were concentrated under reduced pressure and finally freeze-dried to give the n-butanol soluble fraction (F-006) and aqueous fraction (F-007). All the three fractions (A-002, F-006 and F-007) were bioevaluated in different experimental models for peptic ulcer disease.

The following represents the partitioning of the A-002 extract:

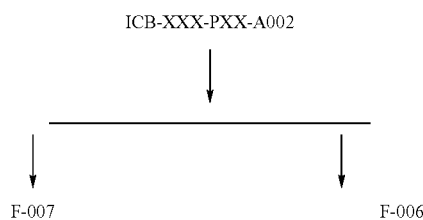

A typical fractionation gave the following result. Air-dried powdered flowers of *Woodfordia fruticosa* (100 g) were extracted with a mixture of methanol and water (250 ml) in the ratio of 1:1 for 18 h. The extraction was repeated twice. The extracts were mixed and concentrated under reduced pressure at 30° C. and finally freeze dried to give a dark-brown powder (20 g) [A-002]. The powdered material is macerated with water (125 ml) and extracted with n-butanol (3×100 ml). The n-butanol extracts are mixed together, washed with water (100 ml), concentrated under reduced pressure and finally freeze-dried to furnish a powder (4 g) [F-006]. In a similar manner the aqueous part is concentrated and freeze dried to give a powdered material (16 g) [F 007].

Example 2

Bioevaluation—Protocols & Results:

The applicant have selected one whole animal model—Cold Restraint Stress Ulcer in Rat (in vivo) to assess ulcer protection capacity of the extracts [Senay E. C. and Levine R. J., *Proc Soc. Exp. Biol. Med.* 124, 1221 (1967)], one isolated stomach model—Chambered Frog Gastric Mucosa (in organ) to assess anti HCl secretion potential [Durbin R. P. and Kircher A. B., *Biochem. Biophys. Acta,* 321, 553 (1973); Ray, T. K. and Tague L. R., *Biochem. Pharmacol.* 29, 2755 (1980); Ray et al., *Proc. Natl. Acad. Sci.* (USA) 79, 1448 (1982)], gastric proton pump inhibition model using pig gastric $H^+$, $K^+$-ATPase-rich apical and tubulovesicular membranes (in vitro) to examine enzyme inhibition [Bandopadhyay, S. Das, P. K., Wright, M. V., Nandi, J., Bhattacharyya, D. and Ray, T. K., *J. Biol. Chem.* 262, 5664 (1987)], and anti *Helicobacter pylori* activity assessment by Disc Diffusion Sensitivity Assay [Glupczynski, Y. In: *Helicobacter pylori: techniques for clinical diagnosis & basic research*, (Eds. Adrian Lee & Francis Megraud), W. B. Saunders Company Ltd., 1996, pp. 17-32].

1. Cold Restraint Stress Ulcer—In vivo Model: This in vivo rat model was used to evaluate stress induced ulcer formation (stress generated by cold as well as restraint) and the effect of pretreatment of the animals with different extracts was examined. Rats, weighing about 200-250 g (either sex), were fasted overnight with ad libitum access to water. About 20-25 mg extracts per kg body weight (suspended in 1:1 methanol-water and sonicated for proper dispersion of insoluble samples) was injected, i. p., prior to stress induction for about 3½-4 h at 4-6$_c$C. About 6-8 rats per batch (control rats received equal volume of vehicle, ~0.2 ml) were used and the data represent average of 4-6 different experiments.

| Extract | Protection % of Ulcer Index (Mean ± SEM) | Mucus |
|---|---|---|
| A-002 | 83.0 ± 4.2 | ++++ |
| F-006 | 90.0 ± 2.9 | +++++ |
| F-007 | 69.0 ± 9.3 | ++++ |

No mortality, either before or during or after stress was noted. The mother extract A-002 appears to be very promising as antiulcer extract. Further, the fraction F-006 appears to be the most potent among the three extracts. The low activity in fraction F-007 indicates that perhaps majority of the active principle is being concentrated in F-006 fraction. The observation was confirmed and reconfirmed with fresh extracts in all three above fractions.

2. Frog Chamber Study: The in organ experiments using the whole frog stomach to assess the anti-HCl secreting potential of extracts and their fractions were carried out employing Frog Chamber Model (for detail about the logic of the experiment and the information to be generated.

1. Frog Chamber Study: The study is based on the principle of 'No Acid No Ulcer'. Since peptic ulcer is invariably accompanied by hyper-secretion of gastric HCl, a study using frog gastric mucosa (*Rana hexadactyla*, available species in West Bengal) as the experimental system was used to generate information about the anti-HCl secreting potential of the extracts vis-à-vis known drugs (omeprazole and/or cimetidine) against histamine stimulated acid secretion. In this in vitro study, frog stomach is mounted in a plastic tube (Using Chamber Study). Employing histamine as the ulcerogen (final common mediator of all the physiological secretagogues), the rate and extent of proton secretion are quantitatively assessed as a function of the amount of herbal preparation and duration of treatment.

The experimental approach, as standardized through a series of experiments with more than 200 plant extracts, has been to measure, over time, (i) basal acid secretion, (ii) histamine-stimulated acid secretion, (iii) extract-induced (two doses) acid secretion, followed by (iv) extract-withdrawn acid secretion. For a particular stomach, after the basal secretion level is known, histamine is inserted from the nutrient side to see maximum acid secreting potential. Thereafter, an extract is inserted (first lower dose and then higher dose) from the nutrient side in presence of continuous supply of histamine to mimic ulcerative situation, followed by withdrawal of the extract by washing the nutrient side with histamine-containing nutrient medium. This latter phase is expected to generate information regarding the efficacy of the extract, upon its withdrawal, towards inhibiting the continuously existing acid secreting phase.

Experiments are carried out with in vitro preparations of gastric mucosa mounted over one end of a plastic tube (mounted area is 1.76 $cm^2$) with the mucosal surface facing out. The mounted tissue is placed vertically inside a 25-ml container. The nutrient solution is regular Frog Ringer solution and the luminal side (secretory side) is bathed in an unbuffered NaCl solution. The volumes of nutrient and mucosal solutions are adjusted in a way so as to be able to maintain constant hydrostatic pressure in the chamber throughout the duration of the experiment. Both solutions are slowly and continuously bubbled with $O_2$ during the entire duration of the experiment. The mucosal solution is slowly and continuously stirred with a magnetic stirrer and collected at 15-min intervals in thoroughly washed clean vials.

In a standardized protocol, 0.1-0.2 mM histamine is used as ulcerogen, while two doses of plant extracts (10 & 50 mg) are used to generate optimum results. Experimentally, each of basal acid secretion, histamine-stimulated acid secretion, drug-induced acid secretion (low followed by high doses) and drug-withdrawn acid secretion are continued for one hour each. The pH of the nutrient sides was monitored over time by accurately measuring the pH values (under $N_2$ bubbled condition), which is a fair reflection of the concentration of proton generated in a particular vial.

Control experiments with two anti-ulcer drugs, namely, cimetidine ($H_2$ receptor blocker) and omeprazole (proton pump inhibitor) were carried out with a series of frog stomach mucosae. The results indicate that under the above-standardized experimental conditions, a concentration of 0.1-0.2 mM of cimetidine (added from nutrient side) or 1-10 mM omeprazole (added from secretory side) is enough to block almost complete acid secretion. This value has been taken to compare the efficacy of various extracts under similar experimental conditions.

In other words, about 0.1-0.2 mM histamine was used as ulcerogen, while two doses of extracts (10 & 50 mg) were used to generate optimum effects. Experimentally, each of basal acid secretion, histamine-stimulated acid secretion, drug-induced acid secretion (low followed by high doses) and drug-withdrawn acid secretion were continued for one hour each. Control experiment with two anti-ulcer drugs, namely, cimetidine ($H_2$ receptor blocker) and omeprazole (proton pump inhibitor) indicated that a concentration of 0.1-0.2 mM of cimetidine (added from nutrient side) or 1-10 mM omeprazole (added from secretory side) could block almost complete acid secretion under the standardized experimental conditions. Quantitative analysis of the results were finally formalized to a qualitative scoring pattern, wherein the rank score for both cimetidine and omeprazole (considered as 100%) were given as +8.

| Extract | Inhibition of Acid Secretion* | Blocking of Reversal of Acid Secretion** | Comment |
|---|---|---|---|
| A-002 | Low/Moderate | Poor/Mild | ++ |
| F-007 | Excellent/Very Good | Good/Excellent | ++++++ |
| F-006 | Moderate/Low | Poor/Mild | 0 |

*Inhibition of the maximum acid secreting potential of histamine-stimulated stomach in presence of low (10 mg) followed by high (50 mg) dose of sample has been graded as Low, Moderate, Very Good and Excellent category.
**Blocking of the Reversal of acid secretion upon withdrawal of sample from the chamber which still contained histamine has been graded as Poor, Mild, Good and Excellent category.

The extract A-002 showed moderate to poor activity when the applicant originally screened different extracts. However, based on other models, when the applicant examined the activities in two fractions, namely, F-006 & F-007, as well as in mother fraction A-002, the applicant surprisingly observed excellent anti HCl secreting potential of the fraction F-007. However, the fraction F-006 continued to show rather moderate potential as far as anti acid secreting potential is concerned. This is an interesting observation of immense scientific curiosity. The observation was confirmed and reconfirmed with fresh extracts in all three above fractions.

3. Anti Gastric Proton Pump Activity Study: Gastric $H^+$, $K^+$-ATPase-rich membranes were prepared from freshly slaughtered pig stomach. These membranes are primarily enriched in tubulovescicular and apical membranes, and showed $K^+$-stimulated activity ($H^+$, $K^+$-ATPase) of around 40 mmoles $P_i$/mg/h with basal activity ($Mg^{2+}$-ATPase) of only around 5-10 mmoles $P_i$/mg/h. An otherwise complete assay mixture containing about 10-15 mg membranes and different amount (1-10 mg) of the extracts were pre-incubated for 10 min before initiating the reaction with substrate ATP. $K^+$-stimulated activity, referred to as $H^+$, $K^+$-ATPase, was calculated as the difference between the activities obtained in presence of $Mg^{2+}$ plus $K^+$ and the basal activity ($Mg^{2+}$-ATPase) in presence of $MG^{2+}$ alone.

| Extract | Concentration (mg/assay) | % Inhibition of $H^+$, $K^+$-ATPase |
|---|---|---|
| A-002 | 10 | 75–90 |
|  | 1 | 60–85 |
| F-006 | 10 | 85–95 |
|  | 1 | 80–90 |
| F-007 | 10 | 80–95 |
|  | 1 | 65–85 |

Omeprazole, the specific inhibitor of gastric $H^+$, $K^+$-ATPase, under this assay condition produces around 50-100% inhibition in the dose range of 0.3-3.0 mg/assay. The extract A-002 showed about 60-85% inhibition at a concentration of 1 mg/assay. Upon further fractionation, while the fraction F-006 showed 80-90% inhibition, the fraction F-007 showed 65-85% inhibition at 1 mg/assay. Notwithstanding the presence of tannins in the extracts and their putative effects on $H^+$, $K^+$-ATPase, it seems logical to conclude that the observed high activity in all three extracts specially in fraction F-006 may be taken to mean that this fraction is perhaps of extreme promise as far as blocking of $H^+$, $K^+$-ATPase in vitro is concerned. The observation was confirmed and reconfirmed with fresh extracts in all three fractions.

4. Anti *H. pylori* Activity—Disc Diffusion Sensitivity Test: The applicant has essentially monitored susceptibility or resistance of *H. pylori* against different concentrations of the extracts by Disc Diffusion Antibiotic Sensitivity Test on a quantitative basis. Two clinically isolated pure strains of *Helicobacter pylori*, one avirulent (strain 80A) and another virulent (strain 121 A), were used for this study. The strains were maintained and cultured under laboratory conditions (Brain Heart Infusion Agar containing 7% FCS, 0.4% each of Isovitalex and *H. pylori* selective Dent). Fresh culture, grown in Brucella Broth containing 5% FCS, was uniformly spread over a selective media plate in which 4 discs (disc diameter 0.5 cm), impregnated with different concentrations of plant extract were placed. The extracts were dissolved in appropriate solvents (water, 50% methanol or methanol) and filter sterilized in case the solvent contained water. Appropriate control experiments with solvents were performed to negate their effects. The plates were kept for about 72 h in a double-gas programmable $CO_2$ Incubator under optimum growth conditions of 5% $O_2$, 10% $CO_2$, 85% $N_2$ and more than 95% humidity. After appropriate time of incubation, the inhibition zone was observed and the zone diameter of each discs was measured.

| Extract | Concentration (mg/disc) | Inhibition Zone Diameter (cm) | |
|---|---|---|---|
| | | 80A | 121A |
| A-002 | 100 | 0.9 | 0.9 |
| | 200 | 1.2 | 1.3 |
| F-006 | 100 | 1.2 | 1.3 |
| | 200 | 1.6 | 1.5 |
| F-007 | 100 | 0.7 | 0.8 |
| | 200 | 1.3 | 1.4 |

The standard antibiotic clarithromycin, at a concentration of 0.5 mg/disc, showed an inhibition zone diameter of around 2.3-2.7 cm. The fraction F-006 is appearing best among all fractions, since it is showing higher zones of inhibition at progressively lower concentrations. Nevertheless, all three fractions showed promising activity. The observation was confirmed and reconfirmed with fresh extracts in all three above fractions.

Summary of Findings and Comments:

(i) In Cold Restraint Stress Ulcer Model (Rat—in vivo), the fraction F-006 showed best protection (about 90%) as compared to parent extract (A-002) and F-007 fraction. By Anti HCl Secretion Potential (Isolated Frog Stomach—In organ) evaluation, the fraction F-007 showed hugely better anti HCl secreting potential as compared to parent extract and F-006 fraction. In Gastric Proton Pump Inhibition studies, the fraction F-006 showed highest potential of about 80-90% inhibition of $H^+$, $K^+$-ATPase activity at 1 mg/assay (omeprazole blocked 50-100% at the concentration range of 0.3-3.0 mg/assay), although both the mother extract (A-002) as well as F-007 fraction showed quite high activity. In Anti *Helicobacter pylori* Activity investigation, the fraction F-006 at a concentration of 200 mg/disc, showed maximum zone of inhibition (disc diameter ~1.5-1.6 cm) as assessed by disc diffusion susceptibility test. However, both the mother extract (A-002) as well as F-007 fraction showed quite high activity. Clarithromycin showed disc diameter of about 2.3-2.7 cm at 0.5 mg/disc with both the strains.

(ii) All the above observations could very well be confirmed and reconfirmed with fresh extracts, albeit with some variations. Repeat experiment with old extracts, showed in general slightly lower activity in majority of the cases, especially in anti *H. pylori* assessment experiments. Nevertheless, the relative strength or weakness of any particular fraction as compared to other two fractions always remained constant.

(iii) Acute toxicity study in mice indicated that all three extracts, namely A-002, F-006 and F-007, are non toxic at a dose of 1 g/kg (p. o.) when observed for 24-h mortality.

(iv) Based on comparison with currently available standard medicines in appropriately employed experimental conditions, the following tentative conclusions may be derived. In terms of anti HCl secretion potential, the relative efficacy of the fraction F-007 comes to about 1:10-20 as compared with cimetidine ($H_2$ receptor blocked), and 1:100 as compared with omeprazole (proton pump inhibitor). In terms of anti $H^+$-pump inhibition studies, the relative efficacy of the fractions (better activity with F-006 fraction) as compared to omeprazole ranges around 1:20-50. In terms of anti *H. pylori* activity, a rough comparison of the MIC values of F-006 and clarithromycin indicates relative efficacy of about 1:500-1000.

(v) This investigation aims at looking into the underlying mechanism(s) of ulceration. Currently available single molecule, like omeprazole (proton pump blocker), cimetidine ($H_2$ receptor blocker), antibiotic like clarithromycin (anti *H. pylori*) are all specifically designed to target those aetiologies which cause ulceration. Our experimental models include targeting the effect on $H_2$ receptor (cimetidine like effect), on gastric proton pump (omeprazole like), on *H. pylori* killing efficiency employing antibiotic sensitivity assay (clarithromycin like) etc. Given the current trend in therapeutic management of peptic ulcer diseases, the applicant have not just mono therapy or double therapy, but triple therapy and even in some cases quadruple therapy. This patent intends to claim the control of majority of the therapeutic potential of the currently prevailing modern medicines by a single plant part.

(vi) During screening exercise, the applicant did observe that different parts of this plant *W. fruticosa* showed quite good anti HCl secreting potential as assessed in Frog Chamber model. The applicant examined three extracts, water, alcohol and 50% alcohol extracts of other parts like stem bark, leaf, root etc. during screening exercise. Some of them, in fact, showed quite good anti HCl secreting potential.

(vii) The plant is easily available in Bengal, Bihar, Orissa and different parts of North-eastern India. Its flowers, however, could only be collected during February-March in a year. Nevertheless, it is not at all difficult to collect lots of 5-10 kg of flower at a time. Considering the approximate yield of about 20 g of A-002 fraction from 100 g of dried flower, it would not be difficult to prepare sufficient quantity for extensive clinical trials, and subsequent formulation for management of human peptic ulcer diseases.

(viii) A rough estimate based on laboratory experimental data on different models used for bioevaluation vis-à-vis comparison with appropriate single molecule modern medicines (see above), and the rules for extrapolation for human dose (16), the applicant anticipate that possibly about 100-200 mg per day would be sufficient for management of human peptic ulcer diseases.

(ix) The plant has been reported to be used as folklore medicine in Indian subcontinent. Also the part flower is credited for the management of diseases like ulcer, haemorrhoids, dysentery, liver diseases, as well as for its reported activity against wound, coughs, microbes like *Helminthosporium sativum* [5], nowhere it has been mentioned for its specific use against ulcers of the stomach and/or duodenum, which encompasses the broad range of a diseases called peptic ulcer diseases. The present investigation specifically aimed at targeting the aetiology of gastric and/or duodenum ulcers by four experimental models covering almost the entire gamut of the pathological criteria of peptic ulcer disease. The term ulcer is a loosely held term encompassing sore or wound in any part, external or internal. In fact, the famous turmeric (*Curcuma longa*) which is reported to be effective against ulcers in general, shows contraindication against gastric ulcer, hyperacidity and peptic ulcer [Sreejayan, N., Rao, M. N. A., *Arzneim Forsch Drug Res.*, 46,169 (1996); Arora, R. B., Basu, N. Kapoor, V., Jain, A. P., *Ind. J. Med. Res.*, 59, 1289 (1971); Kiso, Y., Suzuki, Y., Watnabe, N. *Planta Med.*, 49, 185 (1983)]. Further, research with turmeric (*Curcuma longa*) in people having stomach ulcers has not shown it to be superior to placebo [Van Dau, N., Ngoc Ham, N., Huy Khac, D., *Phytomedicine* 5, 29 (1998); Kositchaiwat, C., Kositchaiwat, S., Havanondha, *J. Med. Assoc.* Thai, 76, 601 (1993]. The same is the case with garlic (*Allium sativum* L.) where it is reported to ameliorate infected wounds, hemorrhoids, antibacterial, but causes adverse effects on gastrointestinal disorders [Morbidoni, L., Arteburnjm, J. M., Young, V., Mullins, D., Mulrow, C. and Lawrence, V., *J. Herbal Pharmacother.* 1, 63 (2001)].

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

REFERENCES

1. Chadha, Y. R. rd., *The wealth of India, Raw materials*, Vol. X (1976), Council of Scientific & Industrial Research, New Delhi pp 586-687
2. Dhar, M. L., Dhar, M. M., Dhawan, B. N., Mehrotra, B. N. and Ray, C., *Ind. J. exp. Biol.* 2, 232 (1968); Paris R. R. and Jacqumin, H., Fitoterapia, 47, 51 (1976).
3. Kadota, S., Takamori, Y., Kikuchi, T., Motegi, A and Ekimoto, H., *Chem. Parm. Bull,* 38, 2687 (1990)
4. Chen, G. L. and Liu, L. F. *Annu. Rep. Medicinal Chemistry,* 21, 257 (1986).
5. Kirtikar, K. R. and Basu, B. D., Indian Medicinal Plants (Eds. Blatter, E., Caius, J. F. and Mhaskar, K. S.), Vol. II, Publishers: Lalit Mohan Basu, Allahabad, India (1935), p. 1074
6. Bhargava, *J. Bombay nat. Hist. Soc.,* 56, 26 (1959); Desai et al. Indian J, Chem. 9, 611 (1971)
7. Hirschowitz, B. L., Keeling, D., Lewin, M., Okabe, S., Parsons, M., Sewing, K. Wallmark, B. and Sachs, G., *Dig. Dis. Sci.,* 40, 3S (1995)
8. Modlin, I. M., *Surg. Gyneol. Obstet.,* 170, 81 (1990)
9. Prinz. C., Kajimura, M., Scott, D., Helander, H., Shin, J., Besancon, M., Bamberg, K., Hersey, S. and Sachs, G., Yale *J. Biol. Med.* 65, 577 (1992)
10. Sachs, G., *Ann. Rev. Pharmacol. Toxicol.,* 28, 269 (1998)
11. Adrian Lee and Francis Megraud (eds) *Helicobacter pylori: techniques for clinical diagnosis & basic research*, W. B. Saunders Company Ltd. 1996
12. Senay E. C. and Levine R. J., *Proc Soc. Exp. Biol. Med.* 124, 1221 (1967)
13. Durbin R. P. and Kircher A. B., *Biochem. Biophys. Acta,* 321, 553 (1973); Ray, T. K. and Tague L. R., *Biochem. Pharmacol.* 29, 2755 (1980); Ray et al., *Proc. Natl. Acad. Sci.* (USA) 79, 1448 (1982)
14. Bandopadhyay, S. Das, P. K., Wright, M. V., Nandi, J., Bhattacharyya, D. and Ray, T. K., *J. Biol. Chem.* 262, 5664 (1987)
15. Glupczynski, Y. In: *Helicobacter pylori: techniques for clinical diagnosis & basic research*, (Eds. Adrian Lee & Francis Megraud), W. B. Saunders Company Ltd., 1996, pp. 17-32
16. Sreejayan, N., Rao, M. N. A., *Arzneim Forsch Drug Res.,* 46,169 (1996); Arora, R. B., Basu, N. Kapoor, V., Jain, A. P., *Ind. J. Med. Res.,* 59, 1289 (1971); Kiso, Y., Suzuki, Y., Watnabe, N. *Planta Med.,* 49, 185 (1983)
17. Van Dau, N., Ngoc Ham, N., Huy Khac, D., *Phytomedicine* 5, 29 (1998); Kositchaiwat, C., Kositchaiwat, S., Havanondha, *J. Med. Assoc.* Thai, 76, 601 (1993)
18. Morbidoni, L., Arteburnjm, J. M., Young, V., Mullins, D., Mulrow, C. and Lawrence, V., *J. Herbal Pharmacother.* 1, 63 (2001)

What is claimed is:

1. A method of treating a subject for an ulcerative condition, said method comprises administering to a subject in need of such treatment a pharmaceutical composition comprising an effective anti-ulcer amount of an aqueous alcoholic extract, or lyophilized aqueous alcoholic extract, of *Woodfordia fruticosa* flowers or at least one bioactive fraction obtained from said lyophilized extract by partitioning it between n-butanol and water and freeze-drying to give a separate n-butanol soluble fraction and a separate aqueous fraction, and one or more pharmaceutically acceptable additives/carriers.

2. A method as claimed in claim 1, wherein the ulcerative condition is caused by at least one member selected from the group consisting of stress-induced ulcer, peptic ulcer, cold restraint induced ulcer, drug induced ulcer and acid induced ulcer.

3. A method as claimed in claim 1, wherein gastric $H^+$, $K^+$-ATPase activity is inhibited.

4. A method as claimed in claim 1, wherein *Helicobacter pylori* activity is inhibited.

5. A method as claimed in claim 1, wherein the subject is a human being or other mammal.

6. A method as claimed in claim 1, wherein the amount of extract administered is in the range of 50 to 200 mg/kg body weight/day.

7. A method as claimed in claim 1, wherein the extract administered is a lyophilized aqueous alcoholic extract.

8. A method as claimed in claim 7, wherein the lyophilized extract is prepared by drying and powdering *Woodfordia fruticosa* flowers to afford powdered flowers, extracting the powdered flowers with a 1:1 mixture of water and alcohol to produce an aqueous alcoholic extract, concentrating the aqueous alcoholic extract and freeze-drying to afford a powder designated as A-002.

9. A method as claimed in claim 8, wherein the amount of the at least one bioactive fraction administered is in the range of 20 to 100 mg/kg body weight/day.

10. A method as claimed in claim 9, wherein the at least one bioactive fraction is prepared by drying and powdering *Woodfordia fruticosa* flowers to afford powdered flowers, extracting the powdered flowers with a 1:1 mixture of water and alcohol to produce an aqueous alcoholic extract, concentrating the aqueous alcoholic extract and freeze-drying to afford a residue, further partitioning the residue with n-butanol and water to obtain two fractions, concentrating the fractions and freeze-drying to give an n-butanol soluble fraction designated as F-006 and an aqueous fraction designated as F-007, and administering at least one of fractions F-006 and F-007, or a mixture of said fractions, to said subject.

11. A method as claimed in claim 1, wherein the composition is in the form of tablets, capsules, or a syrup.

12. A method as claimed in claim 1, wherein the composition is administered orally or intra-muscularly.

13. A method as claimed in claim 1, wherein the subject is in need of therapeutic or prophylactic treatment for peptic ulcer.

14. A method as claimed in claim 1, wherein the composition is administered as a single bolus dose or as a multiple dose.

* * * * *